(12) United States Patent
De Wijs et al.

(10) Patent No.: US 11,832,896 B2
(45) Date of Patent: Dec. 5, 2023

(54) INTERVENTIONAL DEVICE WITH ELECTRICAL CONNECTIONS

(71) Applicant: KONINKLIJKE PHILIPS N.V., Eindhoven (NL)

(72) Inventors: Willem-Jan Arend De Wijs, Oss (NL); Johannes Wilhelmus Weekamp, Beek en Donk (NL); Gerardus Franciscus Cornelis Maria Lijten, Veldhoven (NL); Egbertus Reinier Jacobs, Overloon (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 116 days.

(21) Appl. No.: 17/266,152

(22) PCT Filed: Aug. 2, 2019

(86) PCT No.: PCT/EP2019/070892
§ 371 (c)(1),
(2) Date: Feb. 5, 2021

(87) PCT Pub. No.: WO2020/030548
PCT Pub. Date: Feb. 13, 2020

(65) Prior Publication Data
US 2021/0298841 A1      Sep. 30, 2021

Related U.S. Application Data

(60) Provisional application No. 62/716,134, filed on Aug. 8, 2018.

(30) Foreign Application Priority Data

Oct. 5, 2018   (EP) .................................... 18198759

(51) Int. Cl.
*A61B 34/20* (2016.01)
*A61B 17/34* (2006.01)
(Continued)

(52) U.S. Cl.
CPC ............ *A61B 34/20* (2016.02); *A61B 8/0841* (2013.01); *A61B 17/3403* (2013.01);
(Continued)

(58) Field of Classification Search
CPC ... A61B 34/20; A61B 8/0841; A61B 17/3403; A61B 2017/3413; A61B 2034/2063;
(Continued)

(56) References Cited

U.S. PATENT DOCUMENTS 6,344,037 B1 *   2/2002   Suorsa .................... F16C 1/02
                                              604/528
2004/0111029 A1   6/2004   Bates
(Continued)

FOREIGN PATENT DOCUMENTS

WO    2015155630 A1   10/2015
WO    2015155671 A1   10/2015
(Continued)

OTHER PUBLICATIONS

International Search Report and Written Opinion of PCT/EP2019/070892, dated Oct. 9, 2019.
(Continued)

*Primary Examiner* — Colin T. Sakamoto
*Assistant Examiner* — Tommy T Ly

(57) ABSTRACT

An interventional device includes a sensor interconnection region (101) for making electrical contact to a sensor (102) disposed on the interventional device. The interventional device includes an electrically conductive elongate shaft, a sensor strip (104), electrical conductors (105, 106), and an electrical shield layer (109). The electrical conductors (105,
(Continued)

106) extend along the sensor strip between a sensor region (111) and a window (112) within which the electrical conductors (105, 106) are exposed. The sensor strip (104) is wrapped around the elongate shaft (103) in a spiral such that the electrical conductors (105, 106) extend along the longitudinal axis (A-A') within the window (112), and such that an electrical shield contact portion (109') adjacent the window (112), the window (112), and an exposed portion of the electrically conductive elongate shaft (103') beyond the wrapped sensor strip provide the sensor interconnection region (101).

15 Claims, 2 Drawing Sheets

(51) Int. Cl.
  *A61B 90/00* (2016.01)
  *A61B 8/08* (2006.01)
(52) U.S. Cl.
  CPC ............ *A61B 2017/3413* (2013.01); *A61B 2034/2063* (2016.02); *A61B 2034/2065* (2016.02); *A61B 2090/3786* (2016.02); *A61B 2562/227* (2013.01)
(58) Field of Classification Search
  CPC .......... A61B 2034/2065; A61B 8/4245; A61B 8/4483; A61B 2562/227; A61M 2025/0166; H01L 41/0475
  See application file for complete search history.

(56) References Cited

U.S. PATENT DOCUMENTS

| 2010/0113907 | A1* | 5/2010 | Schwind | A61B 5/14865 |
| | | | | 600/345 |
| 2011/0166455 | A1 | 7/2011 | Cully | |
| 2015/0217090 | A1* | 8/2015 | Burkett | A61B 5/0215 |
| | | | | 600/585 |
| 2017/0033474 | A1* | 2/2017 | Erkamp | H01R 24/58 |
| 2017/0172544 | A1* | 6/2017 | Erkamp | B06B 1/0688 |
| 2017/0172618 | A1 | 6/2017 | Erkamp | |
| 2019/0206589 | A1* | 7/2019 | Sekido | H01B 7/0216 |

FOREIGN PATENT DOCUMENTS

| WO | 2017013224 A1 | 1/2017 | |
| WO | WO-2017013224 A1 * | 1/2017 | ......... A61B 17/3403 |
| WO | WO-2017102369 A1 * | 6/2017 | ......... A61B 17/3403 |
| WO | 2018095793 A1 | 5/2018 | |

OTHER PUBLICATIONS

Mung, Jay et al "A Non-Disruptive Technology for Robust 3D Tool Tracking for Ultrasound-Guided Interventions", MICCAI 2011, Part 1, LNCS 6891, pp. 153-160. Abstact Only.

* cited by examiner

INTERVENTIONAL DEVICE WITH ELECTRICAL CONNECTIONS

CROSS-REFERENCE TO PRIOR APPLICATIONS

This application is the U.S. National Phase application under 35 U.S.C. § 371 of International Application No. PCT/EP2019/070892, filed on Aug. 2, 2019, which claims the benefit of U.S. Provisional Patent Application Ser. No. 62/716,134, filed Aug. 8, 2018 and European Patent Application No. 18198759.5, filed on Oct. 5, 2018. These applications are hereby incorporated by reference herein.

FIELD OF THE INVENTION

The invention relates to an interventional device having a sensor interconnection region. The sensor interconnection region is used to make external electrical contact to a sensor disposed on the interventional device. The interventional device may be used in the medical field in general. The use of a wide range of sensors in various sensing applications is contemplated. In one exemplary application the sensor is an ultrasound sensor that may be used to track the position of the interventional device respective an ultrasound field of a beamforming ultrasound imaging probe.

BACKGROUND OF THE INVENTION

Interventional devices in the medical field increasingly incorporate sensors to gain more information about their surroundings within a patient's anatomy. Sensors of pressure, temperature, fluid flow, sound and ultrasound may for example be incorporated in this regard. In one exemplary application described in more detail in document [1] "A Non-disruptive Technology for Robust 3D Tool Tracking for Ultrasound-Guided Interventions" by Jay Mung, Francois Vignon, and Ameet Jain, in MICCAI 2011, Part I, LNCS 6891, pp. 153-160, 2011, A. Martel, and T. Peters (Eds.), an ultrasound sensor is attached to a medical needle and used to track the position of the needle respective the ultrasound field of a beamforming ultrasound imaging probe.

One issue faced with such interventional devices is the need to provide electrical contact with the sensor.

In this regard, document WO2015155671 discloses a connector that includes an inner conductive body for connecting to a sensor contact on a medical device. An insulator is formed on the inner conductive body. An outer conductive body is formed over the insulator and surrounds the inner conductive body but is electrically isolated from the inner conductive body. The outer conductive body makes contact at two places on a medical device on opposite sides of the inner conductive body.

Another document WO 2015/155630 A1 relates to a needle with thin film piezoelectric sensors. A sensor device includes a flexible planar strip including a plurality of layers. The strip is configured to at least partially encapsulate a medical device. The strip includes a first dielectric layer, a conductive shield layer disposed on the first dielectric layer, a second dielectric layer formed on the conductive shield layer; and a patterned conductive layer including a sensor electrode, a hub electrode and a trace connecting the sensor electrode and the hub electrode.

Another document WO 2017/013224 A1 relates to a transducer laminate. Electrical contact is made between electrical conductors and a transducer layer. The transducer laminate includes two adhesive-coated foils, whose adhesive coatings are arranged to face each other. At a first position along the length of the two electrical conductors the two electrical conductors are sandwiched between the adhesive coatings of the two adhesive-coated foils, and the transducer layer is also sandwiched between the two electrical conductors such that electrical contact is made with the electrodes on the transducer layer. At a second position along the length of the two electrical conductors the two electrical conductors are sandwiched between the adhesive coatings of the two adhesive-coated foils and there is no transducer layer sandwiched between the two electrical conductors.

Despite this progress there remains room to provide improved electrical connections to a sensor disposed on an interventional device.

SUMMARY OF THE INVENTION

The present invention seeks to provide electrical connections to a sensor disposed on an interventional device.

Thereto, an interventional device that includes a sensor interconnection region that is suitable for making electrical contact to a sensor disposed on the interventional device is provided. The interventional device includes an electrically conductive elongate shaft having a longitudinal axis, and a sensor strip that includes the sensor, a first electrical conductor, a second electrical conductor, a first polymer layer, a second polymer layer and an electrical shield layer. The first electrical conductor, second electrical conductor and sensor are disposed between the first polymer layer and the second polymer layer and on a first side of the first polymer layer. The electrical shield layer is disposed on a second side of the first polymer layer. The first electrical conductor and the second electrical conductor are in electrical contact with the sensor and extend along a length direction of the sensor strip between a sensor region that includes the sensor and a window within which the first polymer layer and the electrical shield layer are removed for exposing the first electrical conductor and the second electrical conductor. The electrical shield layer extends along the length direction of the sensor strip between the sensor region and an electrical shield contact portion adjacent the window. The sensor strip is wrapped around the elongate shaft in the form of a spiral such that the electrical shield layer faces outwards, and such that the first electrical conductor and the second electrical conductor both extend along the longitudinal axis within the window, and such that the electrical shield contact portion adjacent the window, the window, and an exposed portion of the electrically conductive elongate shaft beyond the wrapped sensor strip provide the sensor interconnection region.

The electrical conductors within the window, the electrical shield contact portion of the wrapped sensor strip, and the electrically conductive elongate shaft thus provide an electrical interconnection region for the sensor. Advantageously the electrical interconnection region is relatively simple to manufacture since it is provided as a consequence of the spiral-wrapped sensor strip. Moreover, the spiral-wrapped sensor strip provides exposed portions of the first electrical conductor and the second electrical conductor which both extend along the longitudinal axis within the window. This extension, in which the electrical conductors are likewise wrapped in the form of a spiral around the elongate shaft, simplifies the alignment of the electrical conductors with corresponding contacts of an external mating connector because alignment along the longitudinal axis can be achieved by simply rotating the elongate shaft around its longitudinal axis and thereby axially adjusting a contact point on each of the exposed portions of the first electrical conductor and the second electrical conductor along the longitudinal axis.

In accordance with one aspect the electrical shield layer includes a distal end nearest the sensor region and a proximal end adjacent the window. The proximal end is inclined at an acute angle with respect to the length direction of the sensor strip such that when the sensor strip is wrapped around the elongate shaft the proximal end of the electrical shield layer adjacent the window lies in a plane that is normal to the longitudinal axis of the elongate shaft. In so doing, the proximal end of the electrical shield layer adjacent the window does not move along the longitudinal axis of the elongate shaft as the interventional device is rotated. A reference contact point for the electrical shield layer is thus provided at a fixed position along the longitudinal axis. This simplifies the alignment of the electrical shield layer with a corresponding contact of an external mating connector because the electrical shield layer provides a rotationally-invariant contact point.

In accordance with another aspect the sensor strip extends between a distal end nearest the sensor region, and a proximal end nearest the window. The proximal end of the sensor strip is inclined at an acute angle with respect to length direction of the sensor strip such that when the sensor strip is wrapped around the elongate shaft in the form of a spiral the proximal end of the sensor strip lies in a plane that is normal to the longitudinal axis of the elongate shaft. In so doing the proximal end of the wrapped sensor strip terminates in a plane, thereby defining an abutting exposed portion of the conductive elongate shaft that likewise terminates in a plane and does not move along the longitudinal axis of the elongate shaft as the interventional device is rotated. A reference contact point for the conductive elongate shaft is thus provided at a fixed position along the longitudinal axis. This simplifies the alignment of the conductive elongate shaft with a corresponding contact of an external mating connector because the conductive elongate shaft provides a rotationally-invariant contact point.

In accordance with another aspect the interventional device includes an interconnection substrate. The interconnection substrate includes a first contact pad, a second contact pad, and a guard ring. The first contact pad and the second contact pad are separated by a pitch along an interconnection axis for making electrical contact with the first electrical conductor and the second electrical conductor within the window. The guard ring surrounds the first contact pad and the second contact pad and extends along the interconnection axis on both sides of the contact pads for aligning the guard ring with the electrical shield contact portion adjacent the window and the exposed portion of the electrically conductive elongate shaft. Moreover, the interconnection axis is arranged parallel to the longitudinal axis such that the first contact pad and the second contact pad make electrical contact with the first electrical conductor and the second electrical conductor within the window respectively, and such that the guard ring makes electrical contact with both the electrical shield contact portion adjacent the window and the exposed portion of the electrically conductive elongate shaft.

The guard ring thus electrically connects the conductive elongate shaft of the interventional device to the electrical shield layer, on the interconnection substrate. In combination with the electrical shield layer, the guard-ring reduces the susceptibility of the sensor to electromagnetic interference, i.e. EMI. Adequate EMI performance has been achieved even with a planar guard ring in this regard, which obviates the need to completely surround the interconnection region rotationally about the longitudinal axis with an electrical screen. Moreover, connecting the conductive elongate shaft of the interventional device to the electrical shield layer on the interconnection substrate via the guard ring provides a simple means for achieving good EMI performance without having to make such electrical connections on the interventional device itself. Furthermore, consequent to the finding that adequate electrical shielding is provided by such a construction in which the conductive elongate shaft and electrical shield layer are electrically shorted together via the guard ring of the interconnection substrate, a single electrical shield layer may be used in a cable that connects the interconnection substrate to electronic circuitry. The use of a single electrical shield layer in such a cable, rather than one for each of the conductive elongate shaft and the electrical shield layer, reduces its weight and provides increased flexibility.

In accordance with another aspect the interventional device includes an anisotropically conductive elastic layer. The anisotropically conductive elastic layer is disposed between the interconnection substrate and the sensor interconnection region for providing electrical conduction in a radial direction with respect to the elongate axis between the first contact pad and the first electrical conductor, between the second contact pad and the second electrical conductor, and between the guard ring and the electrical shield contact portion adjacent the window and the exposed portion of the electrically conductive elongate shaft beyond the wrapped sensor strip. In so doing, the anisotropically conductive elastic layer, which is conventionally used for attaching planar substrates to planar substrates, is used here to provide a vibration-tolerant means of attaching the interconnection substrate to the sensor interconnection region.

In accordance with another aspect the sensor is an ultrasound sensor and an ultrasound-based position determination system that includes the interventional device is provided. The system benefits from the aforementioned advantages of the interventional device.

Further aspects and their advantages are described with reference to the appended claims. Additional advantages from the described invention will also be apparent to the skilled person.

DETAILED DESCRIPTION OF THE INVENTION

In order to illustrate the principles of the present invention an interventional device in the form of a medical needle is described with particular reference to an exemplary position tracking application in which the sensor is an ultrasound sensor that is used to track the position of the interventional device respective the ultrasound field of a beamforming ultrasound imaging probe.

It is however to be appreciated that the interventional device may also be used in other medical application areas that employ sensors, including blood flow sensing and thermometry. The use of the invention with sensors other than an ultrasound sensor is thus also contemplated, including temperature, sound, optical, pressure and so forth. Moreover, the invention also finds application with other interventional devices than a medical needle, including without limitation a catheter, a guidewire, a biopsy device, a pacemaker lead, an intravenous line or a surgical tool in general. The interventional device may be used in a wide variety or medical procedures, for example from routine needle insertion for regional anesthesia, to biopsies and percutaneous ablation of cancer, and to more advanced interventional procedures.

Figure 1:
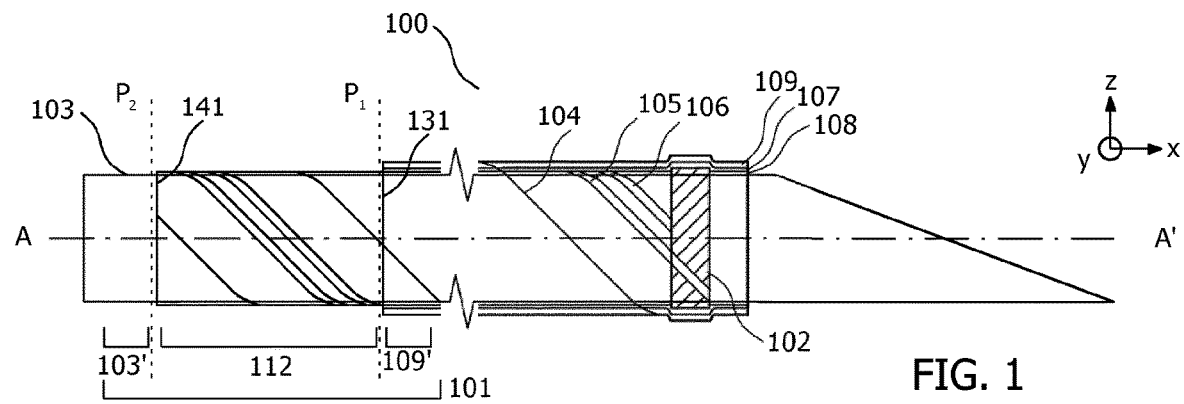
FIG. 1 illustrates a cross-sectional view of an interventional device 100 that includes a sensor 102 and a sensor interconnection region 101 for making electrical contact to the sensor.
Figure 2D:
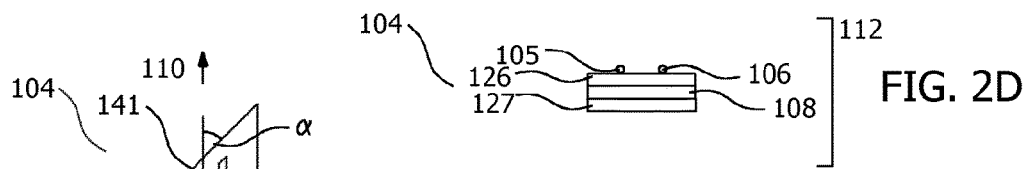
FIG. 2 illustrates various views of a sensor strip 104 that includes sensor 102.
Figure 2B:
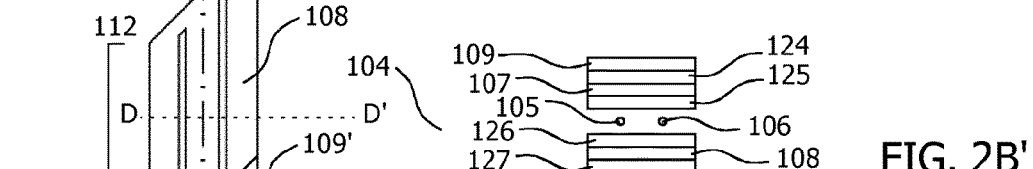
Figure 2B:
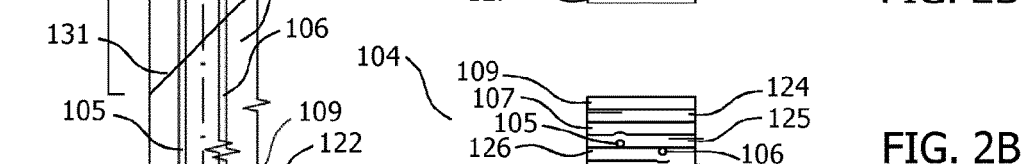
Figure 2C:
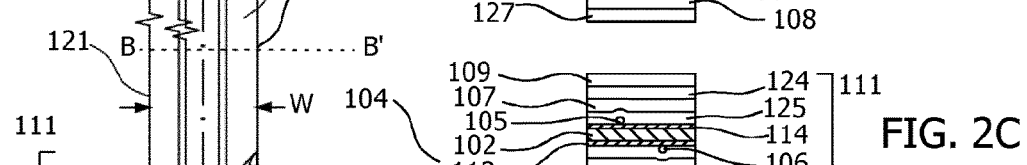
Figure 2C:
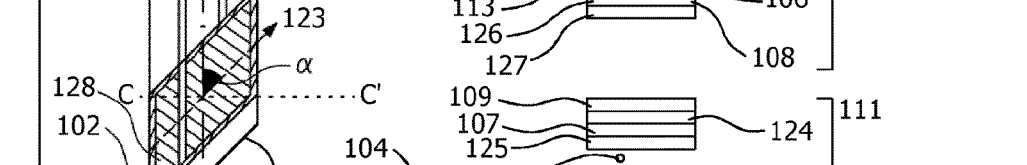
Figure 2A:
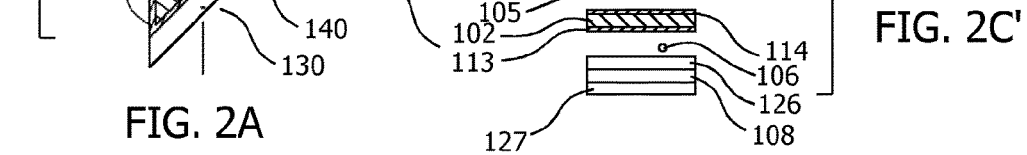

FIG. 1 illustrates a cross-sectional view of an interventional device 100 that includes a sensor 102 and a sensor interconnection region 101 for making electrical contact to the sensor. Interventional device 100 includes electrically conductive elongate shaft 103 having longitudinal axis A-A', and sensor strip that 104 includes sensor 102, a first electrical conductor 105, a second electrical conductor 106, a first polymer layer 107, a second polymer layer 108 and an electrical shield layer 109. With reference to FIG. 2, which illustrates various views of a sensor strip 104 that includes sensor 102; first electrical conductor 105, second electrical conductor 106 and sensor 102 are disposed between first polymer layer 107 and second polymer layer 108 and on a first side of first polymer layer 107. Electrical shield layer 109 is disposed on a second, i.e. opposing side of first polymer layer. In FIG. 2 a plan view of sensor strip 104 is illustrated in FIG. 2A, and sections through sensor strip 104 at B-B', C-C' and D-D' are illustrated in FIGS. 2B, 2C and 2D respectively. Exploded sections through sensor strip 104 at B-B' and C-C' are illustrated in FIGS. 2B' and 2C' respectively. With reference to FIGS. 2A and 2C in particular, first electrical conductor 105, second electrical conductor 106 and sensor 102 are disposed between first polymer layer 107 and second polymer layer 108 and on a first side of first polymer layer 107 in sensor region 111, that includes sensor 102. The first side is lowermost in FIG. 2, and when wrapped around elongate shaft 103 the first side becomes innermost with respect to an opposing second side of first polymer layer 107. Electrical shield layer 109 is disposed on the second, i.e. the opposing side of first polymer layer 107. As seen in particular in FIG. 2C, first electrical conductor 105 and second electrical conductor 106 are in electrical contact with sensor 102 and, as seen in particular in FIG. 2A and FIG. 2D, extend along a length direction 110 of sensor strip between sensor region 111 that includes sensor 102 and a window 112 within which first polymer layer 107 and electrical shield layer 109 are removed for exposing a portion of first electrical conductor 105 and a portion of second electrical conductor 106. As seen in particular in FIG. 2A, electrical shield layer 109 extends along length direction 110 of sensor strip 104 between sensor region 111 and an electrical shield contact portion 109' adjacent window 112. By the term adjacent it is meant abutting, or closest to. Moreover, with reference to FIG. 1, sensor strip 104 is wrapped around elongate shaft 103 in the form of a spiral such that electrical shield layer 109 faces outwards, and such that first electrical conductor 105 and second electrical conductor 106 both extend along longitudinal axis A-A' within window 112, and such that electrical shield contact portion 109' adjacent window 112, window 112, and an exposed portion of electrically conductive elongate shaft 103' beyond the wrapped sensor strip provide sensor interconnection region 101.

As mentioned above, electrical conductors 105, 106 within window 112, electrical shield contact portion 109' of the wrapped sensor strip, and exposed portion of the electrically conductive elongate shaft 103' thus provide an electrical interconnection region for sensor 102. Advantageously electrical interconnection region 101 is relatively simple to manufacture since it is provided as a consequence of spiral-wrapped sensor strip 104. Moreover, spiral-wrapped sensor strip 104 provides exposed portions of first electrical conductor 105 and second electrical conductor 106 which both extend along longitudinal axis A-A' within window 112. Consequent to electrical conductors 105, 106 extending parallel to sensor strip length direction 110, this extension is in the form of a spiral, i.e. a diagonal direction as illustrated in FIG. 1. As used herein, the term parallel refers to angles within +/−5 degrees of exactly parallel. In other words, electrical conductors 106, 106, as with sensor strip 106, become wrapped in the form of a spiral around elongate shaft 103. This simplifies the alignment of electrical conductors 105, 106 with corresponding contacts of an external mating connector because alignment along longitudinal axis A-A' can be achieved by simply rotating elongate shaft 103 around its longitudinal axis and thereby axially adjusting a contact point on each of the exposed portions of the first electrical conductor and the second electrical conductor along the longitudinal axis.

Electrically conductive elongate shaft 103 may for example be provided by the illustrated medical needle, or by a catheter, a biopsy device, a guidewire, a pacemaker lead, an intravenous line or a surgical tool in general. Elongate shaft 103 may in some implementations have circular cross section in a plane that is normal to longitudinal axis A-A'. Electrically conductive elongate shaft 103 may in some implementations be formed from a metal, preferably a metal suitable for surgical applications such as but not limited to type 316 stainless steel.

Sensor 102 may be selected from a range of sensors, including ultrasound, temperature, pressure, flow sensors, optical sensors and so forth. A planar sensor in the form of a band is illustrated in FIG. 1, and in FIG. 2, although the geometry of sensor 102 is not so limited. The use of thin film, thick film, micro electro mechanical structures, i.e. MEMS, or capacitive micromachined ultrasound transducer, i.e. CMUT, sensors is contemplated, as well as the use of multiple sensors, i.e. an array of sensors. These may be wrapped in the form of a band as illustrated in FIG. 1 or individual sensor(s) attached in discrete positions. In one implementation sensor 102 may be a piezoelectric sensor, optionally formed from homopolymer polyvinylidene fluoride, i.e. PVDF, or formed from poly(vinylidene fluoride (VDF)-trifluoroethylene (TrFE)) co-polymer, or formed from lead zirconate titanate, i.e. PZT, and used to detect ultrasound.

Electrical conductors 105, 106 may be formed from a range of materials including gold, copper, silver and aluminium. In some implementations, conductors in the form of a wire is contemplated and in other implementations a planar strip of material is contemplated. Various techniques of electrically contacting electrical conductors 105, 106 with sensor 102 are contemplated, including pressure contact, wire bonding, electrically conducive adhesives and so forth. Preferably, as illustrated in FIG. 2, such contact is pressure contact, and may include electrodes 113, 114 to facilitate such contact. Electrical shield layer 109 may likewise be made from a range of materials including gold, copper, silver and aluminium.

Polymer layers 107, 108 used in sensor strip 104 may be formed from a range of polymers including but not limited to polyethylene terephthalate, PET, polyimide, PI, or polyamide, PA. Moreover, polymer layers 107, 108 may include an adhesive coating, optionally a pressure sensitive adhesive coating, on one or both of their surfaces, these being illustrated as adhesive layers 124, 125, 126, 127 in FIG. 2. The adhesives act to bond each of the polymer layers together. Adhesive layer 127 may be used to attach sensor strip 104 to elongate shaft 103. Pressure sensitive adhesives are a class of materials that form an adhesive bond upon application of pressure. The 3M Corporation, USA is one supplier of suitable pressure sensitive adhesives. These may be supplied as PSA-coated polymer sheets. Polymer layers with PSA on one or both surfaces may be used. PSA-coated polymer sheets are typically provided with a removable release layer that is peeled away to reveal the adhesive coating and thereby protect the adhesive layer until its adhesive properties are required. Sensor strip 104 that is provided by polymer layers 107, 108 preferably has a length that is greater than its width.

With reference to FIG. 2A in particular, electrical shield layer 109 comprises a distal end 130 nearest sensor region 111 and a proximal end 131 adjacent window 112. Optionally, proximal end 131 may be inclined at an acute angle α with respect to length direction 110 of sensor strip 104 such that when sensor strip 104 is wrapped around elongate shaft 103, proximal end 131 of electrical shield layer 109 adjacent window 112 lies in a plane $P_1$ that is normal to longitudinal axis A-A' of elongate shaft 103.

With reference to FIG. 2A, this may be achieved by suitably setting acute angle alpha and the width dimension W of sensor strip 104. Sensor strip 104 includes first edge 121 and opposing second edge 122, these edges being separated by width dimension W. First edge 121 and second edge 122 each extend along length direction 110 of transducer strip 104. Length direction 110 is orthogonal to the direction in which width dimension W is measured. Sensor strip 104 may be wrapped around longitudinal axis A-A' with proximal end 131 of electrical shield layer 109 perpendicular to elongate axis A-A' in order to provide that proximal end 131 of electrical shield layer 109 adjacent window 112 lies in a plane $P_1$ that is normal to longitudinal axis A-A' of elongate shaft 103. The wrapping may be such that adjacent wrapped turns either abut one another, just overlap, or have a gap between one another. In order for consecutive turns of the spiral to abut, i.e. just touch, one another, the following equation should be satisfied:

$$W = \pi \cdot D \cdot \sin(\alpha) \quad \text{Equation 1}$$

wherein α is the acute angle defined above with respect to length direction 110, and D is the diameter of a circular cross section elongate shaft 103. By arranging that W exceeds the above value, consecutive turns of the spiral overlap one another. Likewise by arranging that W is less than this value a small gap may be provided between consecutive turns of the spiral. As mentioned above, by arranging that proximal end 131 of electrical shield layer 109 adjacent window 112 lies in a plane $P_1$ that is normal to longitudinal axis A-A' of elongate shaft 103, proximal end 131 of electrical shield layer 109 adjacent window 109 does not move along longitudinal axis (A-A') of elongate shaft 103 as interventional device 100 is rotated about longitudinal axis A-A'. A reference contact point for electrical shield layer 109 is thus provided at a fixed position along longitudinal axis A-A'. This simplifies the axial alignment of electrical shield layer with a corresponding contact of an external mating connector because electrical shield layer provides a rotationally-invariant contact point.

With reference to FIG. 2A, and FIG. 1, optionally, sensor 102 may be in the form of an elongate strip that extends across width dimension W of sensor strip 104 at acute angle α. In so doing, a sensor may be provided in the form of a band around elongate shaft 103.

With reference to FIG. 2A in particular, sensor strip 104 extends between a distal end 140 nearest sensor region 111 and a proximal end 141 nearest window 112. Optionally, proximal end 141 of sensor strip 104 may be inclined at acute angle α with respect to length direction 110 of sensor strip 104 such that when sensor strip 104 is wrapped around elongate shaft 103 in the form of a spiral, proximal end 141 of sensor strip 104 lies in a plane $P_2$ that is normal to longitudinal axis A-A' of elongate shaft 103.

As mentioned above, in so doing, proximal end 141 of wrapped sensor strip 104 terminates in plane $P_2$, thereby defining an abutting exposed portion of conductive elongate shaft 103 that also terminates in plane $P_2$ and does not move along longitudinal axis A-A' of elongate shaft 103 as interventional device 100 is rotated around longitudinal axis A-A'. A reference contact point for conductive elongate shaft 103 is thus provided at a fixed position along longitudinal axis A-A'. This simplifies the axial alignment of conductive elongate shaft 103 with a corresponding contact of an external mating connector because conductive elongate shaft 103 provides a rotationally-invariant contact point.

Figure 3:
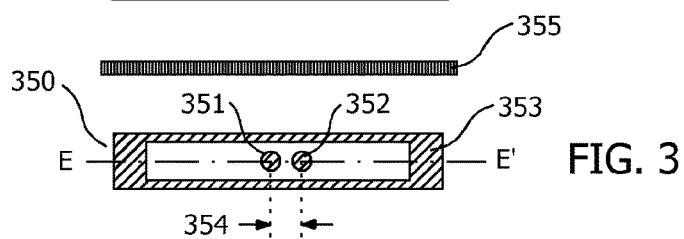
FIG. 3 illustrates an interconnection substrate 350 that includes first contact pad 351 second contact pad 352 and a guard ring 353.

In some implementations, interventional device 100 may be provided with an interconnection substrate for making electrical contact with sensor interconnection region 101. Thereto, FIG. 3 illustrates an interconnection substrate 350 that includes first contact pad 351 second contact pad 352 and a guard ring 353. Optionally interconnection substrate 350 may be planar. Interconnection substrate 350 may for example be provided by a printed circuit board having first contact pad 351 second contact pad 352 and a guard ring 353 disposed on one of its surfaces. With reference to FIG. 3, first contact pad 351 and second contact pad 352 are separated by a pitch 354 along an interconnection axis E-E' that is suitable for making electrical contact with first electrical conductor 105 and second electrical conductor 106 within window 112. Guard ring 353 is disposed on a surface of interconnection substrate 350 and surrounds first contact pad 351 and second contact pad 352 and also extends along interconnection axis E-E' on both sides of contact pads 351, 352 for aligning guard ring 353 with electrical shield contact portion 109' adjacent window 112 and the exposed portion of the electrically conductive elongate shaft 103'. Moreover, interconnection axis E-E' is arranged parallel to longitudinal axis A-A' such that first contact pad 351 and second contact pad 352 make electrical contact with first electrical conductor 105 and second electrical conductor 106 within window 112 respectively, and such that guard ring 353 makes electrical contact with both electrical shield contact portion 109' adjacent window 112 and the exposed portion of the electrically conductive elongate shaft 103'.

Guard ring 353 thus electrically connects conductive elongate shaft 103 of interventional device 100 to electrical shield layer 109, on the interconnection substrate. In combination with electrical shield layer 109, guard-ring 353 reduces the susceptibility of sensor 102 to EMI. Adequate EMI performance has been achieved even with a planar guard ring 353, which obviates the need to completely surround interconnection region 101 rotationally about longitudinal axis A-A' with an electrical screen. Moreover, by connecting conductive elongate shaft 103 of interventional device 102 to electrical shield layer 109 on interconnection substrate 350 via guard ring 353 provides a simple means for achieving good EMI performance without having to make such electrical connections on interventional device 100 itself.

Optionally, as illustrated in FIG. 3, interventional device 100 may include anisotropically conductive elastic layer 355. A suitable layer is marketed by Fujipoly, USA, as a "Zebra elastomeric connector". Anisotropically conductive elastic layer 355 is disposed between interconnection substrate 350 and sensor interconnection region 101 for providing electrical conduction in a radial direction with respect to elongate axis A-A' between first contact pad 351 and first electrical conductor 105, between second contact pad 352 and second electrical conductor 106, and between guard ring 353 and electrical shield contact portion 109' adjacent window 112 and the exposed portion of the electrically conductive elongate shaft 103' beyond the wrapped sensor strip 104. Anisotropically conductive elastic layer 355 may optionally also provide electrical isolation tangentially with respect to a cross section through elongate shaft 103 by means of the use of conductive pillars in layer 355. These arrangements are particularly useful when elongate shaft 103 has a circular cross section in a plane that is normal to longitudinal axis A-A'. As mentioned above, in so doing, anisotropically conductive elastic layer 355, which is conventionally used for attaching planar substrates to planar substrates, is used here to provide a vibration-tolerant means of attaching interconnection substrate 350 to sensor interconnection region 101. This is particularly useful when sensor interconnection region 101 has a curved surface such as that provided by a circular cross section elongate shaft 103.

Interconnection substrate 350 may optionally be provided with an electrical cable, not illustrated. The electrical cable includes a first wire, a second wire and an electrical screen. The electrical screen is arranged around the first wire and the second wire for providing electrical shielding. The first wire is in electrical contact with first contact pad 351, the second wire is in electrical contact with second contact pad 352. The electrical screen is in electrical contact with guard ring 353. It has been found that adequate electrical shielding is provided by the construction in which conductive elongate shaft 103 and electrical shield layer 109 are electrically shorted together via guard ring 353 of interconnection substrate 350. This allows the use of a single electrical shield layer in a cable that connects the interconnection substrate to external electronic circuitry. The use of a single electrical shield layer in such a cable, rather than one for each of the conductive elongate shaft and the electrical shield layer, reduces its weight and provides increased flexibility.

Figure 4:
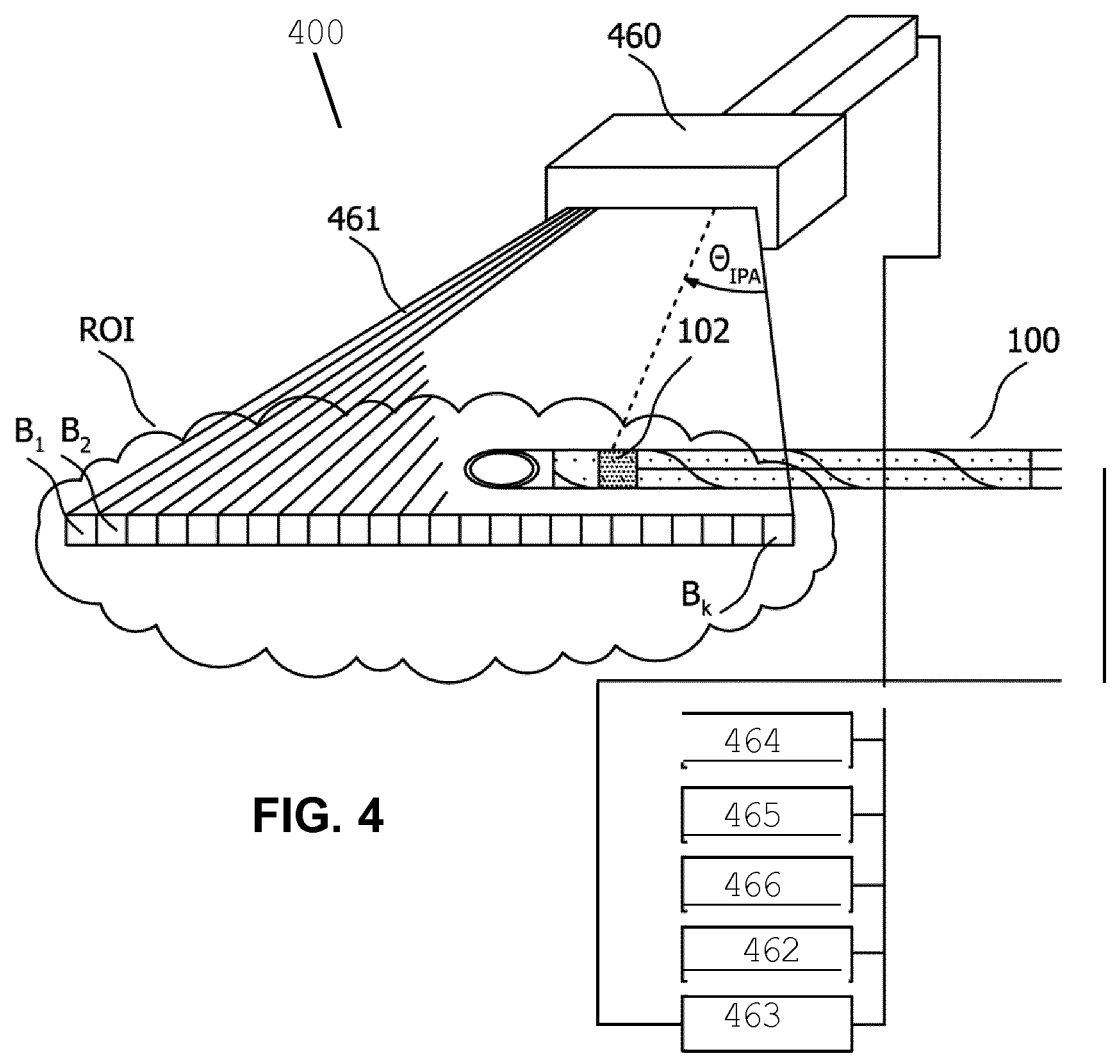
FIG. 4 illustrates an ultrasound-based position determination system 400 that includes interventional device 100.

Interventional device 100 described above finds application in many areas in the medical field. One particular application is now described with reference to FIG. 4, which illustrates an ultrasound-based position determination system 400 that includes interventional device 100. Ultrasound-based position determination system 400 also includes beamforming ultrasound imaging probe 460, image reconstruction unit 462, and position determination unit 463. Sensor 102 in FIG. 4 is an ultrasound sensor. A piezoelectric sensor as described above, or a CMUT, device are non-limiting examples of suitable ultrasound sensors. Beamforming ultrasound imaging probe 460 is configured to generate an ultrasound field 461. Image reconstruction unit 462 is configured to provide a reconstructed ultrasound image corresponding to the ultrasound field 461 of the beamforming ultrasound imaging probe 460. Position determination unit 463 is configured to compute a position of ultrasound sensor 102 of interventional device 100 respective ultrasound field 461 based on ultrasound signals transmitted between beamforming ultrasound imaging probe 460 and ultrasound sensor 102, and to provide an icon in the reconstructed ultrasound image based on the computed position of ultrasound sensor 102. Optional display 464, imaging system interface 465, and imaging system processor 466 illustrated in FIG. 4 may also be included. Links between the various units illustrate their respective communication links.

Together, units 460, 462, 464, 465 and 466 form a conventional ultrasound imaging system. The units 462, 464, 465 and 466 are conventionally located in a console that is in wired or wireless communication with beamforming ultrasound imaging probe 460. Some of units 462, 464, 465 and 466 may alternatively be incorporated within beamforming ultrasound imaging probe 460 as for example in the Philips Lumify ultrasound imaging system. Beamforming ultrasound imaging probe 460 generates ultrasound field 461. In FIG. 4, a 2D beamforming ultrasound imaging probe 460 is illustrated that includes a linear ultrasound transceiver array that transmits and receives ultrasound energy within an ultrasound field 461 which intercepts region of interest ROI. The ultrasound field is fan-shaped in FIG. 4 and includes multiple ultrasound beams $B_{1 \ldots k}$ that together provide the illustrated image plane. Note that whilst FIG. 4 illustrates a fan-shaped beam the invention is not limited to use with a particular shape of ultrasound field or indeed to a planar ultrasound field. Beamforming ultrasound imaging probe 460 may also include electronic driver and receiver circuitry, not shown, that is configured to amplify and/or to adjust the phase of signals it transmits or receives in order to generate and detect ultrasound signals in ultrasound beams $B_{1 \ldots k}$.

In-use the above-described conventional ultrasound imaging system is operated in the following way. An operator may plan an ultrasound procedure via imaging system interface 465. Once an operating procedure is selected, imaging system interface 465 triggers imaging system processor 466 to execute application-specific programs that generate and interpret the signals transmitted to and detected by beamforming ultrasound imaging probe 460. A memory, not shown, may be used to store such programs. The memory may for example store ultrasound beam control software that is configured to control the sequence of ultrasound signals transmitted by and/or received by beamforming ultrasound imaging probe 460. Image reconstruction unit 462 provides a reconstructed ultrasound image corresponding to ultrasound field 461 of beamforming ultrasound imaging probe 460. Image reconstruction unit 462 thus provides an image corresponding to the image plane defined by ultrasound field 461 and which intercepts region of interest ROI. The function of image reconstruction unit 462 may alternatively be carried out by imaging system processor 466. The image may subsequently be displayed on display 464. The reconstructed image may for example be an ultrasound Brightness-mode "B-mode" image, otherwise known as a "2D mode" image, a "C-mode" image or a Doppler mode image, or indeed any ultrasound image.

Also shown in FIG. 4 is interventional device 100, exemplified by a medical needle, which includes ultrasound sensor 102. In this exemplary application, interventional device 102, or more specifically ultrasound sensor 102 disposed thereon, may be tracked respective ultrasound field 461 based on signals provided by position determination unit 463. Position determination unit is in communication with units 460, 462, 464, 465 and 466, i.e. the conventional ultrasound imaging system, as illustrated by the interconnecting links. Position determination unit 463 is also in communication with ultrasound sensor 102, which communication may for example be wired or wireless. The function of position determination unit 463 may in some implementations be carried out by a processor of the conventional ultrasound imaging system.

In-use, the position of ultrasound sensor 102 is computed respective ultrasound field 461 by position determination unit 463 based on ultrasound signals transmitted between beamforming ultrasound imaging probe 460 and ultrasound sensor 102. Ultrasound sensor 102 detects ultrasound signals corresponding to beams $B_{1...k}$. Position determination unit 463 identifies the position of ultrasound sensor 102 based on i) the amplitudes of the ultrasound signals corresponding to each beam $B_{1...k}$ that are detected by ultrasound sensor 102, and based on ii) the time delay, i.e. time of flight, between emission of each beam $B_{1...k}$ and its detection by ultrasound sensor 102. Position determination unit 463 subsequently provides an icon in the reconstructed ultrasound image based on the computed position of ultrasound sensor 102. The icon may for example indicate the computed position of ultrasound sensor 102. The icon may optionally also indicate a range of positions within which a portion of the interventional device, e.g. its distal end, may lie. More specifically the position is computed by finding the best fit position of ultrasound sensor 102 respective ultrasound field 461 based on the detected ultrasound signals.

This may be illustrated as follows. When ultrasound sensor 102 is in the vicinity of ultrasound field 461, ultrasound signals from the nearest of beams $B_{1...k}$ to the sensor will be detected with a relatively larger amplitude whereas more distant beams will be detected with relatively smaller amplitudes. Typically the beam that is detected with the largest amplitude is identified as the one that is closest to ultrasound sensor 102. This beam defines in-plane angle $\theta_{IPA}$ between beamforming ultrasound imaging probe 460 and ultrasound sensor 102. The corresponding range depends upon the time delay, i.e. the time of flight, between the emission of the largest-amplitude beam $B_{1...k}$ and its subsequent detection. The range may thus be determined by multiplying the time delay by the speed of ultrasound propagation. Thus, the range and corresponding in-plane angle $\theta_{IPA}$ of the beam detected with the largest amplitude can be used to identify the best-fit position of ultrasound sensor 102 respective ultrasound field 461.

Various examples of the disclosure are enumerated below:

Example 1

Interventional device (100) comprising a sensor interconnection region (101) for making electrical contact to a sensor (102) disposed on the interventional device; the interventional device comprising:
- an electrically conductive elongate shaft (103) having a longitudinal axis (A-A'); and
- a sensor strip (104) comprising the sensor (102), a first electrical conductor (105), a second electrical conductor (106), a first polymer layer (107), a second polymer layer (108) and an electrical shield layer (109);
- wherein the first electrical conductor (105), the second electrical conductor (106) and the sensor (102) are disposed between the first polymer layer (107) and the second polymer layer (108) and on a first side of the first polymer layer (107); and wherein the electrical shield layer (109) is disposed on a second side of the first polymer layer (107);
- wherein the first electrical conductor (105) and the second electrical conductor (106) are in electrical contact with the sensor (102) and extend along a length direction (110) of the sensor strip between a sensor region (111) that includes the sensor (102) and a window (112) within which the first polymer layer (107) and the electrical shield layer (109) are removed for exposing the first electrical conductor (105) and the second electrical conductor (106); and
- wherein the electrical shield layer (109) extends along the length direction (110) of the sensor strip (104) between the sensor region (111) and an electrical shield contact portion (109') adjacent the window (112); and
- wherein the sensor strip (104) is wrapped around the elongate shaft (103) in the form of a spiral such that the electrical shield layer (109) faces outwards, and such that the first electrical conductor (105) and the second electrical conductor (106) both extend along the longitudinal axis (A-A') within the window (112), and such that the electrical shield contact portion (109') adjacent the window (112), the window (112), and an exposed portion of the electrically conductive elongate shaft (103') beyond the wrapped sensor strip provide the sensor interconnection region (101).

Example 2

The interventional device (100) according to Example 1 wherein the electrical shield layer (109) comprises a distal end (130) nearest the sensor region and a proximal end (131) adjacent the window (112), wherein the proximal end (131) is inclined at an acute angle ($\alpha$) with respect to the length direction (110) of the sensor strip (104) such that when the sensor strip is wrapped around the elongate shaft (103) the proximal end (131) of the electrical shield layer (109) adjacent the window lies in a plane ($P_1$) that is normal to the longitudinal axis (A-A') of the elongate shaft (103).

Example 3

The interventional device (100) according to Example 1 wherein the sensor strip (104) extends between a distal end (140) nearest the sensor region (111), and a proximal end (141) nearest the window (112); wherein the proximal end of the sensor strip is inclined at an acute angle ($\alpha$) with respect to length direction (110) of the sensor strip such that when the sensor strip is wrapped around the elongate shaft (103) in the form of a spiral the proximal end (141) of the sensor strip lies in a plane ($P_2$) that is normal to the longitudinal axis (A-A') of the elongate shaft (103).

Example 4

The interventional device according to Example 1 further comprising an interconnection substrate (350), the interconnection substrate comprising:
- a first contact pad (351);
- a second contact pad (352); and
- a guard ring (353);
- wherein the first contact pad (351) and the second contact pad (352) are separated by a pitch (354) along an interconnection axis (E-E') for making electrical contact with the first electrical conductor (105) and the second electrical conductor (106) within the window (112);

wherein the guard ring (353) surrounds the first contact pad (351) and the second contact pad (352) and extends along the interconnection axis (E-E') on both sides of the contact pads (351, 352) for aligning the guard ring (353) with the electrical shield contact portion (109') adjacent the window (112) and the exposed portion of the electrically conductive elongate shaft (103');

wherein the interconnection axis (E-E') is arranged parallel to the longitudinal axis (A-A') such that the first contact pad (351) and the second contact pad (352) make electrical contact with the first electrical conductor (105) and the second electrical conductor (106) within the window (112) respectively, and such that the guard ring (353) makes electrical contact with both the electrical shield contact portion (109') adjacent the window (112) and the exposed portion of the electrically conductive elongate shaft (103').

Example 5

The interventional device according to Example 4 further comprising an anisotropically conductive elastic layer (355);

wherein the anisotropically conductive elastic layer (355) is disposed between the interconnection substrate (350) and the sensor interconnection region (101) for providing electrical conduction in a radial direction with respect to the elongate axis (A-A') between the first contact pad (351) and the first electrical conductor (105), between the second contact pad (352) and the second electrical conductor (106), and between the guard ring (353) and the electrical shield contact portion (109') adjacent the window (112) and the exposed portion of the electrically conductive elongate shaft (103') beyond the wrapped sensor strip.

Example 6

The interventional device according to Example 4 or Example 5 further comprising an electrical cable, the electrical cable comprising a first wire, a second wire and an electrical screen;

wherein the electrical screen is arranged around the first wire and the second wire for providing electrical shielding;

wherein the first wire is in electrical contact with the first contact pad (351);

wherein the second wire is in electrical contact with the second contact pad (352);

wherein the electrical screen is in electrical contact with the guard ring (353).

Example 7

The interventional device according to Example 1 wherein the sensor (102) is an ultrasound sensor.

Example 8

The interventional device according to Example 1 wherein the elongate shaft (103) is provided by a medical needle.

Example 9

Ultrasound-based position determination system (400) comprising:
an interventional device (100) according to Example 1 wherein the sensor (102) is an ultrasound sensor;
a beamforming ultrasound imaging probe (460) configured to generate an ultrasound field (461);
an image reconstruction unit (462) configured to provide a reconstructed ultrasound image corresponding to the ultrasound field (461) of the beamforming ultrasound imaging probe (460);
a position determination unit (463) configured to compute a position of the ultrasound sensor (102) of the interventional device (100) respective the ultrasound field (461) based on ultrasound signals transmitted between the beamforming ultrasound imaging probe (460) and the ultrasound sensor (102), and to provide an icon in the reconstructed ultrasound image based on the computed position of the ultrasound sensor (102).

Whilst reference has been made above to a planar ultrasound imaging probe in the above it is to be appreciated that the exemplified beamforming ultrasound imaging probe 460 is only one example of a beamforming ultrasound imaging probe in which interventional device 100 may be used. Interventional device 100 also finds application in ultrasound-based position determination systems that include other types of 2D or 3D beamforming ultrasound imaging probes. These may include for example a "TRUS" transrectal ultrasonography probe, an "IVUS" intravascular ultrasound probe, a "TEE" transesophageal probe, a "TTE" transthoracic probe, a "TNE" transnasal probe, an "ICE" intracardiac probe. Moreover, it is to be appreciated that interventional device 100 also finds application in other ultrasound sensing applications in the medical field beyond position tracking.

Any of the method steps disclosed herein, particularly those described in relation to the processor of position determination unit 463 may be recorded in the form of instructions which when executed on a processor cause the processor to carry out such method steps. The instructions may be stored on a computer program product. The computer program product may be provided by dedicated hardware as well as hardware capable of executing software in association with appropriate software. When provided by a processor, the functions can be provided by a single dedicated processor, by a single shared processor, or by a plurality of individual processors, some of which can be shared. Moreover, explicit use of the term "processor" or "controller" should not be construed to refer exclusively to hardware capable of executing software, and can implicitly include, without limitation, digital signal processor "DSP" hardware, read only memory "ROM" for storing software, random access memory "RAM", non-volatile storage, etc. Furthermore, embodiments of the present invention can take the form of a computer program product accessible from a computer-usable or computer-readable storage medium providing program code for use by or in connection with a computer or any instruction execution system. For the purposes of this description, a computer-usable or computer readable storage medium can be any apparatus that may include, store, communicate, propagate, or transport the program for use by or in connection with the instruction execution system, apparatus, or device. The medium can be an electronic, magnetic, optical, electromagnetic, infrared, or semiconductor system, or apparatus or device, or a propagation medium. Examples of a computer-readable medium include a semiconductor or solid state memory, magnetic tape, a removable computer diskette, a random access memory "RAM", a read-only memory "ROM", a rigid magnetic disk and an optical disk. Current examples of optical disks include compact disk-read only memory "CD-ROM", compact disk-read/write "CD-R/W", Blu-Ray™ and DVD.

In summary, an interventional device has been provided that includes a sensor interconnection region 101 for making electrical contact to a sensor 102 disposed on the interventional device. The interventional device includes an electrically conductive elongate shaft, a sensor strip 104, electrical conductors 105, 106, and an electrical shield layer 109. The electrical conductors 105, 106 extend along the sensor strip between a sensor region 111 and a window 112 within which the electrical conductors 105, 106 are exposed. The sensor strip 104 is wrapped around the elongate shaft 103 in a spiral such that the electrical conductors 105, 106 extend along the longitudinal axis A-A' within the window 112, and such that an electrical shield contact portion 109' adjacent the window 112, the window 112, and an exposed portion of the electrically conductive elongate shaft 103' beyond the wrapped sensor strip provide the sensor interconnection region 101.

Various embodiments and options have been described in relation to the interventional device, and it is noted that the various embodiments may be combined to achieve further advantageous effects. Any reference signs in the claims should not be construed as limiting the scope of the invention.

As recited herein, the term "or" should be interpreted as a disjunctive "or." Further, the term "or" and the term "and" when prefaced by the term "at least one of" or the term "one or more of" should be interpreted as a disjunctive list such that, for example, a list of "at least one of A or B" or a list of "one or more of A and B" or a list of "A or B" should be interpreted to include either A or B, one of A and one of B, a combination of one or more of each of A and B; both A and B; or combinations of one or more of A and one or more of B, and such other combinations as relevant to the recited list or terms consistent with the corresponding description in the specification.

The invention claimed is:

1. An interventional device comprising:
    an electrically conductive elongated shaft having a longitudinal axis; and
    a sensor strip wrapped around the electrically conductive elongated shaft in a form of a spiral, the sensor strip comprising a sensor, a first electrical conductor, a second electrical conductor, a first polymer layer, a second polymer layer, a window, and an electrical shield layer that are arranged on the sensor strip to align the first electrical conductor and the second electrical conductor to corresponding contacts of an external mating connector,
    wherein the first electrical conductor, the second electrical conductor, and the sensor are disposed between the first polymer layer and the second polymer layer on a first side of the first polymer layer,
    wherein the electrical shield layer is disposed on a second side of the first polymer layer and facing outwards from the electrically conductive elongated shaft,
    wherein the first electrical conductor and the second electrical conductor are in electrical contact with the sensor and a length of the first electrical conductor and the second electrical conductor extending parallel to a length direction of the sensor strip between (i) a sensor region, at a distal end of the sensor strip, that includes the sensor, and (ii) a proximal end of the window at a proximal end of the sensor strip,
    wherein the sensor strip includes the window that extends on the sensor strip along a portion of the length of the first electrical conductor and the second electrical conductor lying between a proximal end of the electrical shield layer and a proximal end of the first electrical conductor and the second electrical conductor, the window corresponding to a portion of the sensor strip with the first polymer layer and the electrical shield layer removed to expose the first electrical conductor and the second electrical conductor,
    wherein the electrical shield layer extends on the sensor strip along another portion of the length of the first electrical conductor and the second electrical conductor lying between the sensor region and a distal end of the window, and
    wherein the sensor strip includes a sensor interconnection region comprising the electrical shield contact portion adjacent the window, the window, and an exposed portion of the electrically conductive elongated shaft beyond the wrapped sensor strip, and
    wherein the electrical shield layer extends on the sensor strip with the proximal end of the electrical shield layer inclined at an acute angle with respect to the length direction of the sensor strip, and the electrical shield layer is disposed on the electrically conductive elongated shaft with the proximal end of the electrical shield layer lying in a plane that is normal to the longitudinal axis of the electrically conductive elongated shaft.

2. The interventional device according to claim 1, wherein the proximal end of the sensor strip is inclined at an acute angle with respect to the length direction of the sensor strip such that the wrapped sensor strip positions the proximal end of the sensor strip to lie in a plane that is normal to the longitudinal axis of the electrically conductive elongated shaft.

3. The interventional device according to claim 1, further comprising an interconnection substrate, the interconnection substrate comprising:
    a first contact pad;
    a second contact pad; and
    a guard ring,
    wherein the first contact pad and the second contact pad are separated by a pitch along an interconnection axis for making electrical contact with the first electrical conductor and the second electrical conductor within the window,
    wherein the guard ring surrounds the first contact pad and the second contact pad and extends along the interconnection axis on both sides of the contact pads for aligning the guard ring with the electrical shield contact portion adjacent the window and the exposed portion of the electrically conductive elongated shaft,
    wherein the interconnection axis is arranged parallel to the longitudinal axis such that the first contact pad and the second contact pad make electrical contact with the first electrical conductor and the second electrical conductor within the window respectively, and such that the guard ring makes electrical contact with both the electrical shield contact portion adjacent the window and the exposed portion of the electrically conductive elongated shaft.

4. The interventional device according to claim 3, further comprising an anisotropically conductive elastic layer,
    wherein the anisotropically conductive elastic layer is disposed between the interconnection substrate and the sensor interconnection region for providing electrical conduction in a radial direction with respect to the longitudinal axis between the first contact pad and the first electrical conductor, between the second contact pad and the second electrical conductor, and between the guard ring and the electrical shield contact portion adjacent the window and the exposed portion of the electrically conductive elongated shaft beyond the wrapped sensor strip.

5. The interventional device according to claim 3, further comprising an electrical cable, the electrical cable comprising a first wire, a second wire and an electrical screen,
wherein the electrical screen is arranged around the first wire and the second wire and is configured to provide electrical shielding,
wherein the first wire is in electrical contact with the first contact pad,
wherein the second wire is in electrical contact with the second contact pad, and
wherein the electrical screen is in electrical contact with the guard ring.

6. The interventional device according to claim 1, wherein the sensor is an ultrasound sensor.

7. The interventional device according to claim 1, wherein the electrically conductive elongated shaft comprises a medical needle.

8. An ultrasound-based position determination system comprising:
an interventional device according to claim 1 wherein the sensor is an ultrasound sensor;
a beamforming ultrasound imaging probe configured to generate an ultrasound field; and
a processor configured to provide a reconstructed ultrasound image corresponding to the ultrasound field of the beamforming ultrasound imaging probe, and to compute a position of the ultrasound sensor of the interventional device relative to the ultrasound field based on ultrasound signals transmitted between the beamforming ultrasound imaging probe and the ultrasound sensor, and to provide an icon in the reconstructed ultrasound image based on the computed position of the ultrasound sensor.

9. A system for providing electrical contact to a sensor, the system comprising:
an interventional device with an electrically conductive elongated shaft having a longitudinal axis; and
a sensor strip configured to be wrapped around the electrically conductive elongated shaft in a form of a spiral, the sensor strip comprising the sensor, one or more electrical conductors, a window, and an electrical shield layer that are arranged on the sensor strip, such that when the sensor strip is wrapped around the electrically conductive elongated shaft, a first electrical conductor and a second electrical conductor align to corresponding contacts of an external mating connector,
wherein the one or more electrical conductors are in electrical contact with the sensor and a length of the one or more electrical conductors extend parallel to a length direction of the sensor strip between (i) a sensor region, at a distal end of the sensor strip, that includes the sensor and (ii) a proximal end of the window at a proximal end of the sensor strip,
wherein the sensor strip includes the window that extends on the sensor strip along a portion of the length of the first electrical conductor and the second electrical conductor lying between a proximal end of the electrical shield layer and a proximal end of the first electrical conductor and the second electrical conductor, the window corresponding to a region with the electrical shield layer removed to expose the one or more electrical conductors,
wherein the electrical shield layer extends on the sensor strip along another portion of the length of the first electrical conductor and the second electrical conductor lying between a distal end of the window,
wherein, the sensor strip is configured such that, when the sensor strip is wrapped around the electrically conductive elongated shaft in the form of the spiral with the one or more electrical conductors extending along the longitudinal axis within the window, the window, the electrical shield contact portion, and an exposed portion of the electrically conductive elongated shaft provide a sensor interconnection region configured to provide an electrical contact to the sensor, and
wherein the electrical shield layer extends on the sensor strip with the proximal end of the electrical shield layer inclined at an acute angle with respect to the length direction of the sensor strip, such that when the sensor strip is wrapped around the electrically conductive elongated shaft in the form of the spiral with the distal end positioned nearest the sensor region and the proximal end positioned adjacent the window, the proximal end of the electrical shield layer lies in a plane that is normal to the longitudinal axis of the electrically conductive elongated shaft.

10. The system according to claim 9, wherein the proximal end of the sensor strip is inclined at an acute angle with respect to the length direction of the sensor strip such that, when the sensor strip is wrapped around the electrically conductive elongated shaft in the form of the spiral, the proximal end of the sensor strip lies in a plane that is normal to the longitudinal axis of the electrically conductive elongated shaft.

11. The system according to claim 9, further comprising an interconnection substrate, the interconnection substrate comprising:
a first contact pad;
a second contact pad; and
a guard ring,
wherein the first contact pad and the second contact pad are separated by a pitch along an interconnection axis for making electrical contact with the one or more electrical conductors within the window,
wherein the guard ring surrounds the first contact pad and the second contact pad and extends along the interconnection axis on both sides of the contact pads for aligning the guard ring with the electrical shield contact portion adjacent the window and the exposed portion of the electrically conductive elongated shaft,
wherein the interconnection axis is arranged parallel to the longitudinal axis such that the first contact pad and the second contact pad make electrical contact with the one or more electrical conductors within the window, and such that the guard ring makes electrical contact with both the electrical shield contact portion adjacent the window and the exposed portion of the electrically conductive elongated shaft.

12. The system according to claim 11, further comprising an anisotropically conductive elastic layer,
wherein the anisotropically conductive elastic layer is disposed between the interconnection substrate and the sensor interconnection region for providing electrical conduction in a radial direction with respect to the longitudinal axis between the first contact pad and a first electrical conductor of the one or more electrical conductors, between the second contact pad and a second electrical conductor of the one or more electrical conductors, and between the guard ring and the electrical shield contact portion adjacent the window and the exposed portion of the electrically conductive elongated shaft beyond the wrapped sensor strip.

13. The system according to claim 11, further comprising an electrical cable, the electrical cable comprising a first wire, a second wire and an electrical screen,
- wherein the electrical screen is arranged around the first wire and the second wire and is configured to provide electrical shielding,
- wherein the first wire is in electrical contact with the first contact pad, wherein the second wire is in electrical contact with the second contact pad, and
- wherein the electrical screen is in electrical contact with the guard ring.

14. The system according to claim 9, wherein the sensor is an ultrasound sensor.

15. The system according to claim 9, wherein the electrically conductive elongated shaft comprises a medical needle.

* * * * *